US00PP20204P3

(12) United States Plant Patent
Rasmussen

(10) Patent No.: US PP20,204 P3
(45) Date of Patent: Aug. 4, 2009

(54) *SCHLUMBERGERA* PLANT NAMED 'SAMBA BRAZIL'

(50) Latin Name: *Schlumbergera truncata*
Varietal Denomination: SAMBA BRAZIL

(75) Inventor: Lau Lindegaard Rasmussen, Kerteminde (DK)

(73) Assignee: Rohde's A/S, Kerteminde (DK)

( * ) Notice: Subject to any disclaimer, the term of this patent is extended or adjusted under 35 U.S.C. 154(b) by 0 days.

(21) Appl. No.: 12/082,787

(22) Filed: Apr. 14, 2008

(65) Prior Publication Data

US 2009/0070905 P1 Mar. 12, 2009

(51) Int. Cl.
*A01H 5/00* (2006.01)

(52) U.S. Cl. ..... Plt./372

(58) Field of Classification Search ..... Plt./372
See application file for complete search history.

*Primary Examiner*—June Hwu
(74) *Attorney, Agent, or Firm*—Foley & Lardner LLP

(57) ABSTRACT

A new and distinct *Schlumbergera* plant named 'SAMBA BRAZIL' particularly characterized by large upright to vertical flowers, with less reflexing of petals; flowers which have petals which are red-purple (RHS 58A) in color at the edges, color transitioning to orange (RHS 27D) and then white (RHS N155B) at the center of petal, and with a white (RHS N155C) throat; large quantity of flowers per plant; moderately vigorous growth rate and fairly compact, freely branching growth habit; and ovoid to lanceolatoid buds red-purple (RHS N66A) in color.

4 Drawing Sheets

Latin name of the genus and species of the plant claimed: *Schlumbergera truncata,*
Variety denomination: 'SAMBA BRAZIL'.

BACKGROUND OF THE INVENTION

The present invention relates to a new and distinct cultivar of *Schlumbergera* plant, botanically known as *Schlumbergera truncata* (Haworth) Moran., commonly known as Thanksgiving Cactus, and hereinafter referred to by the cultivar name 'SAMBA BRAZIL'.

*Schlumbergera* (formerly *Zygocactus*) of the Cactaceae family consists of 6 known species which are epiphytic cacti and native to Brazil. Common names for *Schlumbergera* plants include: Crab Cactus for the cultivar's claw-like phylloclade margin, Thanksgiving Cactus for cultivars which bloom in November, and Christmas Cactus for cultivars which bloom in December.

The new *Schlumbergera* cultivar is a product of a planned breeding program conducted by the inventor, Lau Lindegaard RASMUSSEN, in Fyn, Demark. The objective of the breeding program was to develop a new *Schlumbergera* cultivar with excellent branching habit and large, upright flowers with a unique color combination.

The new *Schlumbergera* cultivar originated from an outcrossing made by the. inventor, Lau Lindegaard RASMUSSEN, in 2001 in Fyn, Demark. The female or seed parent is the *Schlumbergera truncata* 'SALSA DANCER' (unpatented, disclosed in EU-CPVO No. 2004/1247). The male or pollen parent is an *Schlumbergera truncata* '8620A' (unpatented). The new *Schlumbergera* cultivar was discovered and selected by the inventor as a single flowering plant within the progeny of the stated outcrossing in a controlled environment in 2003 in Fyn, Denmark, on the basis of its flower color and its fairly compact and freely branching habit. Plants of the new *Schlumbergera* are more upright, and have a unique color combination of the flowers combined with healthy, shiny green phyllocladia and excellent branching.

Asexual reproduction of the new *Schlumbergera* cultivar by phylloclade cuttings, followed by trial production batches, was first performed in January of 2004 in Fyn, Denmark, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'SAMBA BRAZIL' which in combination distinguish this *Schlumbergera* as a new and distinct cultivar:

1. Large upright to vertical flowers, with less reflexing of petals;
2. Flowers which have petals which are red-purple (RHS 58A) in color at the edges, color transitioning to orange (RHS 27D) and then white (RHS N 155B) at the center of petal, and with a white (RHS N 155C) throat;
3. Large quantity of flowers per plant;
4. Moderately vigorous growth rate and fairly compact, freely branching growth habit; and
5. Ovoid to lanceolatoid buds red-purple (RHS N66A) in color.

Plants of the new *Schlumbergera truncata* 'SAMBA BRAZIL' differ from plants of the female parental cultivar, *Schlumbergera truncata* 'SALSA DANCER' (unpatented, disclosed in EU-CPVO No. 2004/1247) in the following characteristics:

1. Plants of 'SAMBA BRAZIL' have a petal color combination of red-purple lobe edges (RHS 58A) with transition zone of orange (RHS 27D) to white (RHS 155B) at center and a white (RHS 155C) tube color whereas plants of 'SALSA DANCER' have a petal color combination of red-purple lobe edges (RHS 71C) with a white center (RHS 155A) and a white (RHS 155C) tube color;
2. Plants of 'SAMBA BRAZIL' have less reflexing petals than plants of 'SALSA DANCER';
3. Plants of 'SAMBA BRAZIL' produce longer (3.7 cm to 4.2 cm) and lighter green (RHS 137C) phyllocladia whereas plants of 'SALSA DANCER' produce shorter (3.4 cm to 4.0 cm) and dark green (RHS 138A) phyllocladia;
4. Plants of 'SAMBA BRAZIL' have undulating to curly phyllocladia margins whereas plants of 'SALSA DANCER' have flat phyllocladia margins;
5. Plants of 'SAMBA BRAZIL' are taller (about 21 cm) than plants of 'SALSA DANCER' (about 17 cm); and
6. Plants of 'SAMBA BRAZIL' produce more flowers and buds per plant (about 30 to 40) whereas plants of 'SALSA DANCER' produce less flowers and buds per plant (about 25 to 35).

Plants of the male parental cultivar, *Schlumbergera truncata* '8620A' (unpatented), are not available to provide a botanical comparison to plants of the new *Schlumbergera truncata* 'SAMBA BRAZIL'.

Of the many commercial cultivars known to the present inventor, the most similar in comparison to the new *Schlumbergera* 'SAMBA BRAZIL' is the female parental cultivar, *Schlumbergera truncata* 'SALSA DANCER', as described above.

BRIEF DESCRIPTION OF THE PHOTOGRAPHS

The accompanying photographs illustrate the overall appearance of the new *Schlumbergera* cultivar 'SAMBA BRAZIL' showing the colors as true as is reasonably possible with colored reproductions of this type. Colors in the photographs may differ slightly from the color values cited in the detailed botanical description, which accurately describe the color of 'SAMBA BRAZIL'.

DETAILED BOTANICAL DESCRIPTION

Figure 1:
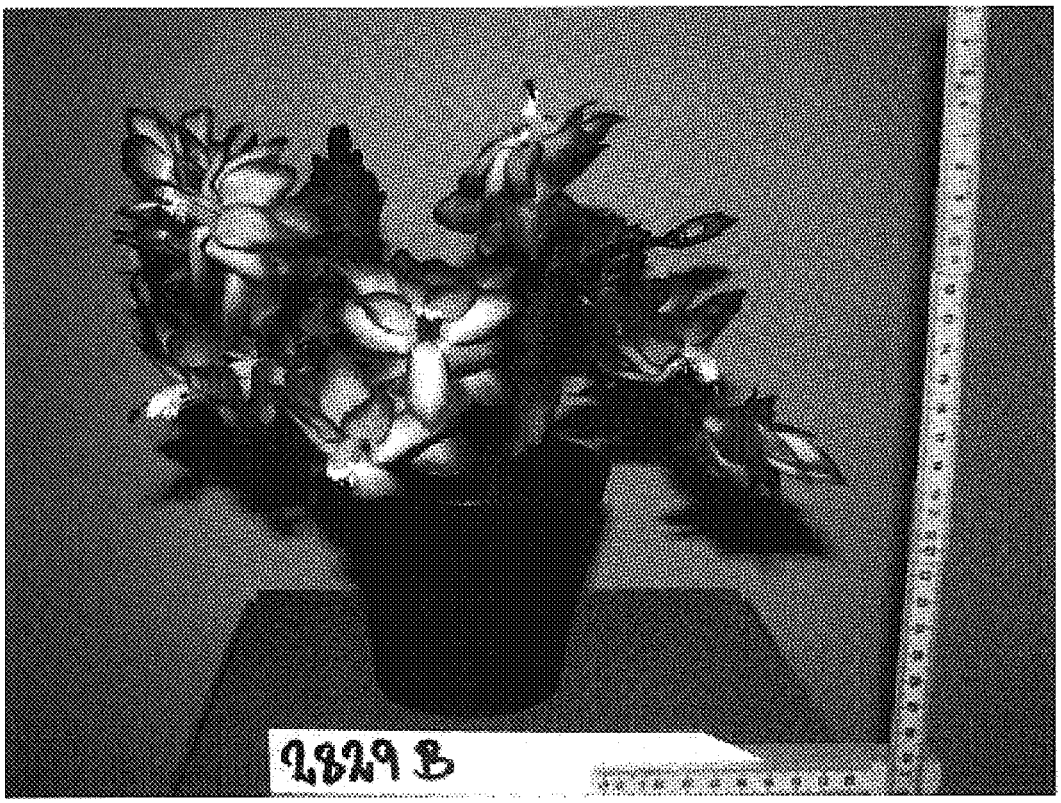
FIG. 1 shows a side perspective view of a typical flowering plant of 'SAMBA BRAZIL' (identified by breeder's reference no. 2829B) grown in a 9.0 cm pots, at 10 to 11 months of age.
Figure 2:
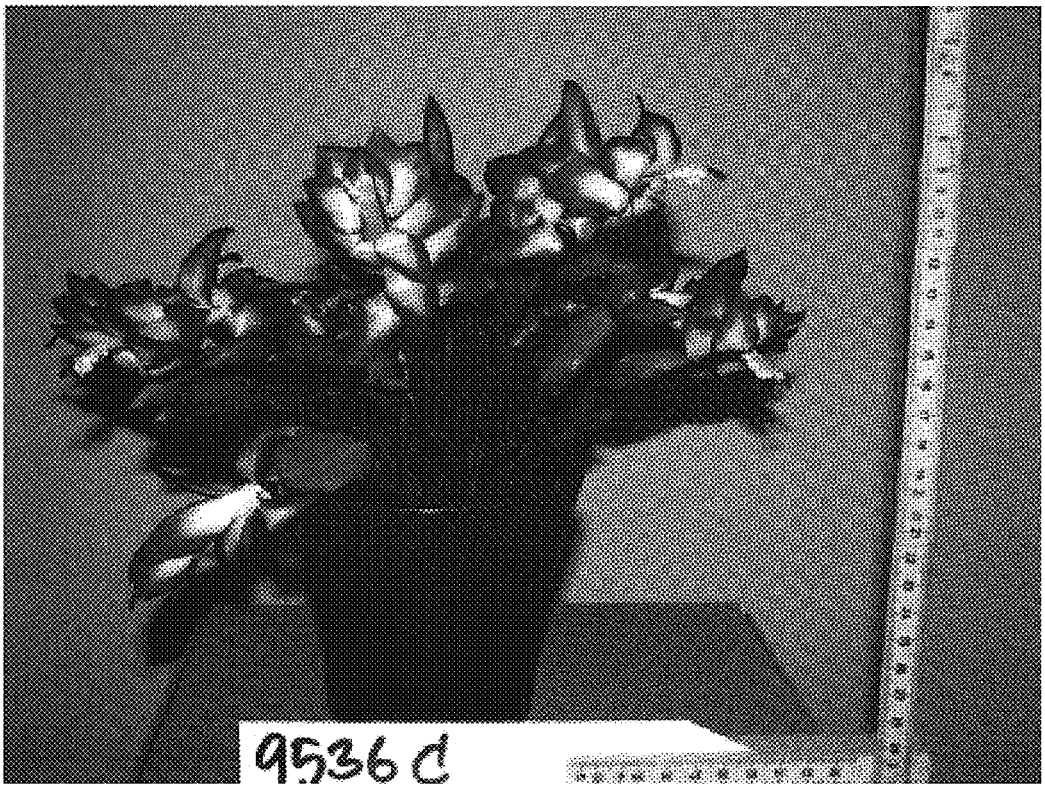
FIG. 2 shows a side perspective view of a typical flowering plant of female parental and comparison cultivar 'SALSA DANCER' (identified by breeder's reference no. 9536C) grown in a 9.0 cm pots, at 10 to 11 months of age.
Figure 3:
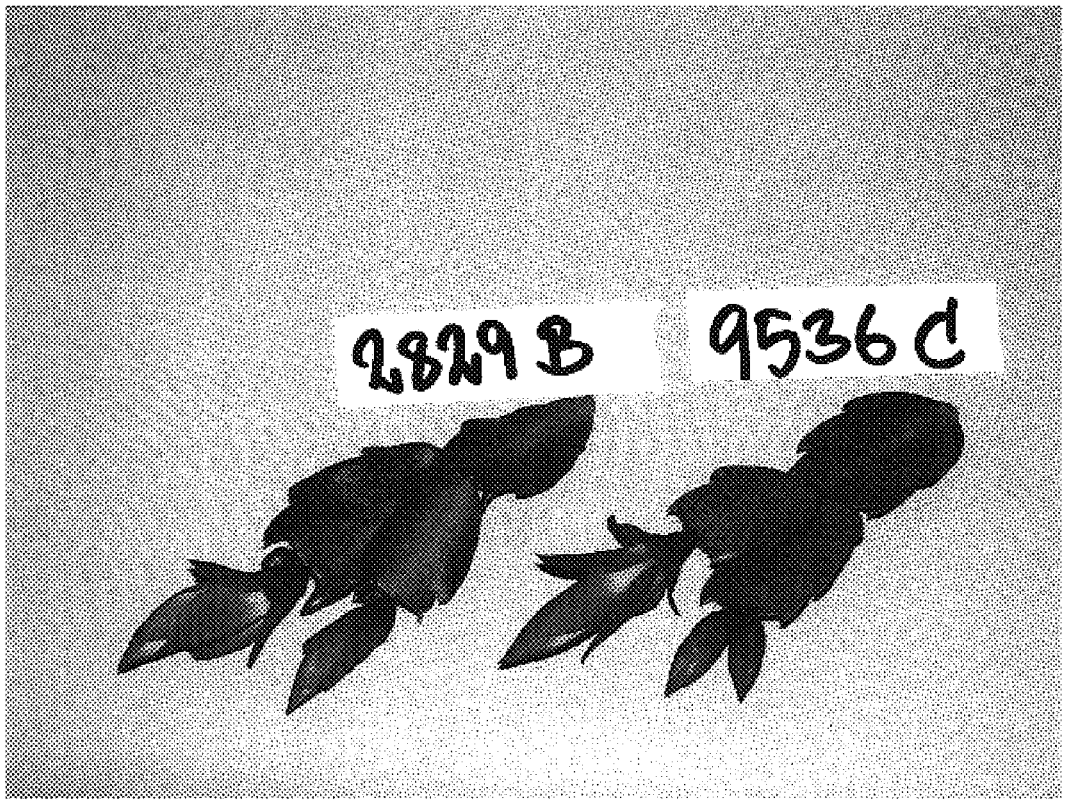
FIG. 3 shows a close-up comparison view of typical immature (not opened) flowers and phyllocladia of 'SAMBA BRAZIL' (identified by breeder's reference no. 2829B) and typical immature (not opened) flowers and phyllocladia of 'SALSA DANCER' (identified by breeder's reference no. 9536C) at 10 to 11 months of age.
Figure 4:
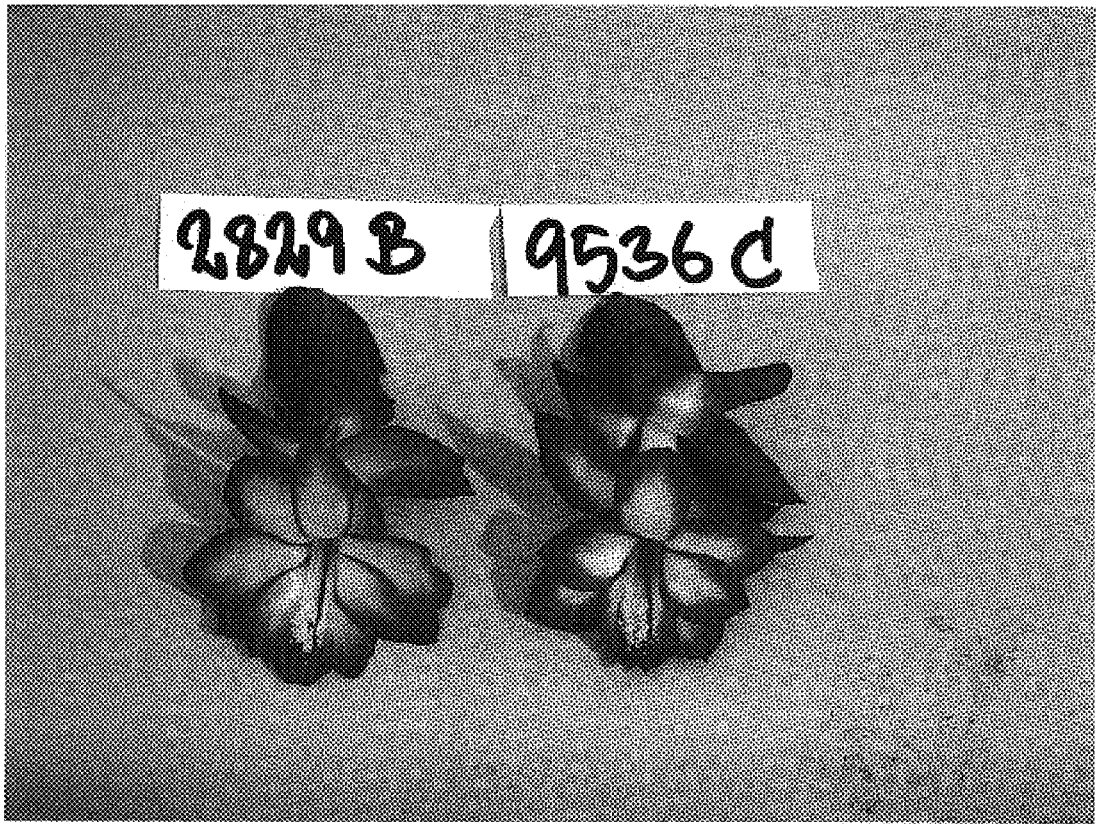
FIG. 4 shows a close-up comparison view of typical mature (fully opened) flowers and phyllocladia of 'SAMBA BRAZIL' (identified by breeder's reference no. 2829B) and mature (fully opened) flowers and phyllocladia of 'SALSA DANCER' (identified by breeder's reference no. 9536C) at 10 to 11 months of age.

The new *Schlumbergera* cultivar 'SAMBA BRAZIL' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'SAMBA BRAZIL' as grown in a glass-covered greenhouse in Fyn, Denmark, under conditions which closely approximate those generally used in commercial practice. Plants of 'SAMBA BRAZIL' are themo-photoperiodic and will develop buds and bloom best under short day conditions (less than 12 hours of sunlight for a period of 4 weeks). Plants of 'SAMBA BRAZIL' are grown under an average day temperature of 18° C. and an average night temperature of 16° C. Ambient light levels of +50 W m-2 were used and no growth retardants were applied when growing plants of 'SAMBA BRAZIL'.

Color references are made to The Royal Horticultural Society Colour Chart (R.H.S.), $4^{th}$ edition, except where general colors of ordinary significance are used. The photographs and descriptions were taken during the Fall of 2007 in Fyn, Denmark, when outdoor day temperatures averaged 18° C. and outdoor night temperatures averaged 16° C. The age of the plants described is about 40 weeks after cutting.

Classification:
- *Botanical.*—*Schlumbergera truncata.*
- *Common name.*—Thanksgiving Cactus.

Parentage:
- *Female or seed parent.*—*Schlumbergera truncata* 'SALSA DANCE' (unpatented, disclosed in EU-CPVO No. 2004/1247).
- *Male or pollen parent.*—*Schlumbergera truncata* '8620A' (unpatented).

Propagation: By single, mature phylloclade cuttings.
- *Time and temperature to initiate roots.*—In a greenhouse, about 30 days at 18° C. to 21° C.
- *Time and temperature to produce a rooted cutting.*—In a greenhouse, about 50 days at 18° C. to 21° C.
- *Rooting habit and description.*—Fine, well-branched and RHS 155A, white in color.

Plant:
- *Type.*—Perennial, Epiphyte.
- *Growth habit.*—Overall upright and becoming pendent as lateral branches lengthen.
- *Branching habit.*—Freely branching, with two or three new phylloclades forming at the apical of older phylloclades.
- *Vigor.*—Slow growth rate.
- *Crop time.*—After rooting, about 10 months are required to produce a finished flowering plant in an 9 cm pot.
- *Size at maturity.*—Height (soil level to top of plant, including flowers): About 21 cm. Spread: About 23 cm to 25 cm.

Stem: None, older phylloclades may turn woody with age (several years).

Lateral branches:
- *Arrangement.*—Phylloclades form at the apical end of older phylloclades to form branches.
- *Quantity.*—About 6 to 7.

*Length.*—Primary: About 4.5 cm (1 phylloclade). Secondary: About 7 cm to 9 cm (2 to 3 phylloclades).
*Width.*—About 4 cm to 5 cm.
*Aspect.*—Upright to arching (from basal phylloclade).
*Strength.*—Strong (from basal phylloclade).
*Appearance.*—Glabrous and smooth.
*Pubescence.*—None.
*Color.*—Green, RHS N137A.

Phylloclade:
*Arrangement.*—Single and sequential.
*Quantity per lateral branch.*—About 8 to 9.
*Length.*—About 3.7 cm to 4.2 cm.
*Width.*—About 3.0 cm to 3.5 cm.
*Thickness.*—About 4 mm to 5 mm (at center vein of phylloclade).
*Overall shape.*—Oblong to rotund.
*Apex shape.*—Truncate with 2–4 protruding marginal teeth (about 6 mm to 8 mm in length), forming a claw-like shape.
*Base shape.*—Rounded.
*Margin.*—Undulating and Serrated; about 2–4 teeth (5–7 mm in length).
*Texture.*—Glabrous, smooth.
*Color of upper surface.*—Immature: Green, RHS 137C. Mature: Green, RHS 137A. Margin: Green, RHS 137A.
*Color of under surface: Immature: Green, RHS* 137D. Mature: Green, RHS 137A. Margin: Green, RHS 137A.
*Venation.*—Pattern: Costate. Color (Upper and Under Surfaces): Green, RHS 137A.

Areole: Not true areole structure; tip of phylloclade is barbellate, 4–6 short hairs or bristles.

Inflorescence description:
*Arrangement and appearance.*—Single, double or triple sessile flowers borne on apical end of phylloclades. Flowers are hose-in-hose and zygomorphic. When mature flowers are fully open, they form a right angle to the phylloclade. Flowers persistent; petals fold and wither slowly.
*Natural flowering season.*—Flowering occurs from October to January (northern hemisphere), but can be changed by short day photo-treatments.
*Flowering response time.*—About 10 weeks from planting.
*Rate of flowers opening.*—About 4 per week, depending on temperature and light.
*Flowering longevity* (*dependent on temperature and light conditions*).—About 5 to 6 days.
*Fragrance.*—None.
*Quantity of flowers per lateral branch.*—About 3 to 5.
*Quantity of buds per lateral branch.*—About 2.
*Quantity of lowers and buds per plant.*—About 30 to 40.
*Flower bud.*—Length: About 4.5 cm to 5.5 cm (before anthesis). Width: About 1.3 cm to 1.4 cm (before anthesis). Shape: Lanceolatoid with mucronate tip. Color: Red-purple, RHS N66A.
*Flower.*—Type: Single. Shape: Tubular, hose-in-hose triple perianth. Aspect: Initially facing upward, later facing outward (right angle to phylloclade). Persistent or self-cleaning: Persistent, but drops after withering.
*Corolla size.*—Depth: About 7.0 cm (including ovary). Diameter: About 7.0 cm. Tube length: About 30 mm. Tube diameter: About 9 mm.
*Petals.*—Quantity: Apical Whorl: About 8 to 9; Basal whorl: About 5. Length: About 2.7 cm to 3.5 cm Width: About 1.8 cm to 2.0 cm Shape: Obovate. Apex: Rounded to obtuse. Base: Apical Whorl: Fused; Basal Whorl: Free. Margin: Entire. Appearance: Shiny Texture: Silky (both surfaces). Color (when opening, both upper and under surfaces): Petals: Red-purple, RHS 58A, transitioning to orange, RHS 27D, with white, RHS N 155B, center; Petal Margin: Red-purple, RHS 58A; Tube: White, RHS N155C. Color (when fully opened, both upper and under surfaces): Petals: Red-purple, RHS 58A, transitioning to orange, RHS 27D, with white, RHS N 155B, center; Petal Margin: Red-purple, RHS 58A; Tube: White, RHS N155C. Color fading: None.
*Petaloids.*—Appearance: Same as petals. Arrangement: Free. Quantity: About 7 to 9. Length: Up to 1.5 cm. Width: About 0.7 cm to 1.0 cm. Shape: Ovate. Apex: Acute. Base: Free or Fused. Margin: Entire. Texture (both surfaces): Silky. Color (immature and mature, upper and under surfaces): Red-purple, RHS N66A.
*Sepals.*—Appearance: Same as petals. Arrangement: Free. Quantity: About 5. Length: About 0.5 cm to 0.7 cm. Width: About 0.5 cm. Shape: Ovate. Apex: Acute. Base: Truncate. Margin: Entire. Texture (both surfaces): Glabrous. Color (immature and mature, upper and under surfaces): Overall: Red-purple, RHS N66B; Margin: Red-purple, RHS 58A.

Reproductive organs:
*Androecium.*—Stamen: Quantity: About 20 to 40 polyandrous, phaenantherous, incurved. Some filaments fused to perianth tube (connate). Length: About 45 mm. Color: White, RHS 155D, translucent. Anther: Shape: Basifixed, ovoid. Length: About 1 mm. Color: Light yellow, RHS 11C. Filament: Length: About 50 mm to 60 mm. Color: White, RHS 155D, translucent. Pollen: Amount: Abundant. Color: Light yellow, RHS 11C.
*Gynoecium.*—Pistil: Quantity: 1. Shape: Slightly curved. Length: About 70 mm. Stigma: Shape: Claw-like. Color: Red-purple, RHS N74A. Style: Length: About 67 mm. Color: Red-purple, RHS N74A. Ovary: Shape: Angular. Length: About 4 to 5 mm. Width: About 5 mm. Color: Greyed-orange, RHS 175A.

Seeds/fruit: None observed.

Disease/pest resistance: No test for disease/pest resistance have been performed yet.

Disease/pest susceptibility: No test for disease/pest resistance have been performed yet.

Temperature tolerance: Tolerant to a low temperature of about +2° C. and to a high temperature about +40° C.

I claim:

1. A new and distinct *Schlumbergera* plant named 'SAMBA BRAZIL', as illustrated and described herein.

* * * * *